United States Patent [19]

Doherty et al.

[11] Patent Number: 4,717,722

[45] Date of Patent: Jan. 5, 1988

[54] SUBSTITUTED 1-OXA-DETHIACEPHALOSPORINS AS ANTI-INFLAMMATORY AND ANTIDEGENERATIVE AGENTS

[75] Inventors: James B. Doherty, New Milford; William K. Hagmann, Westfield, both of N.J.

[73] Assignee: Merck & Co., Inc, Rahway, N.J.

[21] Appl. No.: 607,536

[22] Filed: May 7, 1984

[51] Int. Cl.$^4$ .................. A61K 31/395; A61K 31/535
[52] U.S. Cl. .................................. 514/210; 514/234; 514/886; 514/914
[58] Field of Search ............... 514/232, 210, 234, 886, 514/914

[56] References Cited

U.S. PATENT DOCUMENTS

| | | | |
|---|---|---|---|
| 4,123,528 | 11/1978 | Cama et al. | 514/232 |
| 4,197,402 | 4/1980 | Hamashima et al. | 544/90 |
| 4,271,159 | 1/1981 | Hannah | 514/230 |
| 4,296,111 | 10/1981 | Beattie et al. | 514/201 |
| 4,342,758 | 8/1982 | Firestone | 514/201 |

FOREIGN PATENT DOCUMENTS 0023602 9/1977 Japan.
1455016 11/1976 United Kingdom.

OTHER PUBLICATIONS

Aoki et al., Tetrahedron Letters, No. 44, pp. 4327-4330, 1979.
Chem Abstr., 102(17):148985v, 1985.

*Primary Examiner*—J. R. Brown
*Assistant Examiner*—John W. Rollins
*Attorney, Agent, or Firm*—Theresa Y. Cheng; Michael C. Sudol

[57] ABSTRACT

Substituted 1-oxa-dethiacephalosporins are found to be effective elastase inhibitors and thereby useful anti-inflammatory/antidegenerative agents.

4 Claims, No Drawings

SUBSTITUTED 1-OXA-DETHIACEPHALOSPORINS AS ANTI-INFLAMMATORY AND ANTIDEGENERATIVE AGENTS

BACKGROUND OF THE INVENTION

We have found that substituted 1-oxa-dethiacephalosporins are potent elastase inhibitors and therefore are useful anti-inflammatory/antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelburg, New York, pp. 196–206, 1979.

Accordingly, an object of this invention is to discover new protease inhibitors, especially elastase inhibitors, useful for controlling tissue damage and various inflammatory or degenerative conditions mediated by proteases particularly elatase.

Another object of the present invention is to provide pharmaceutical compositions for administering the active substituted 1-oxa-dethia cephalosporins as protease inhibitors.

Still a further object of this invention is to provide a method of controlling inflammatory conditions by administering a sufficient amount of one or more of the active, substituted 1-oxa-dethiacephalosporins in a mammalian species in need of such treatment.

DETAILED DESCRIPTION OF THE INVENTION

A. Scope of the Invention

This invention relates to 1-oxa-dethiacephalosporins as potent elastase inhibitors useful in the prevention, control and treatment of inflammatory conditions especially arthritis and emphysema.

Most of the 1-oxa-dethiacephalosporins are known antibiotics which have been described, for example, in U.S. Pat. Nos. 4,296,111, 4,123,528, 4,167,630, 4,226,866, 4,150,156, 4,271,159; EPO patent Nos. 25,857, 18,595; German patent Nos. 2355-209, and 2355-210; and Belgium patent No. 857621.

The 1-oxa-dethiacephalosporins of the present invention are of formula:

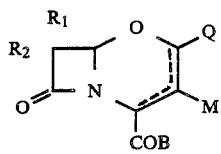
(I)

wherein M is:

(1) H;
(2) halo such as chloro or fluoro;
(3) —COOR wherein R represents H, loweralkyl, phenyl or benzyl;
(4) —CHO;
(5) —CH$_2$A wherein A represents
  (a) hydrogen;
  (b) halo;
  (c) hydroxy;
  (d) alkoxy especially loweralkoxy of 1 to 6 carbons such as methoxy, ethoxy, n- or i-propoxy, n- or t-butoxy;
  (e) aryloxy especially phenoxy;
  (f) aralkyloxy especially benzyloxy;
  (g) —SR;

(h)

(i) acyloxy especially alkanoyloxy or arylcarbonyloxy such as acetoxy, benzyloxycarbonyloxy, benzoyloxy; and succinoyloxy; substituted or unsubstituted carbamoyl, thiocarbamoyl and N-alkyl or N,N-dialkyl derivatives thereof;
(j) unsubstituted or substituted amino or amido group especially —NH$_2$, —CONH$_2$ and N-alkyl or N,N-dialkyl derivatives thereof;
(k) CN;
(l) loweralkyl;

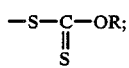
(m)

(n) heterocyclothio especially

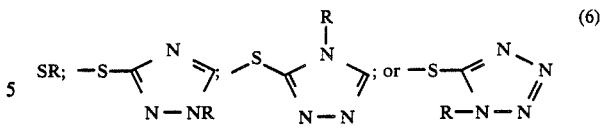
(6)

(7)

wherein n is 0–2, X is halo, C$_{1-3}$ alkanoyloxy, toluene-sulfonyloxy, benzenesulfonyloxy, trifluoroacetoxy, p-nitrobenzoyloxy, or p-nitrophenoxy, and Y is H, C$_{1-3}$ alkyl;

(8) trifluoromethyl;
(9) OR;
(10) alkenyloxy;
(11) arylthio; or
(12) aryl sulfonyloxy.

Preferably, M is CH$_2$A where A represents
(a) hydrogen;
(b) F or Cl;
(c) hydroxy;
(d) C$_{1-3}$ alkoxy;

(e)

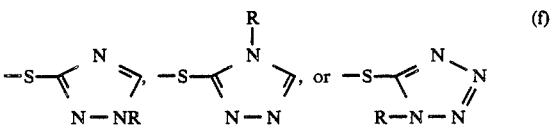
(f)

(g) alkanoyloxy; or

(h)

More preferably, M is CH$_2$A wherein A is
(a) alkanoyloxy especially

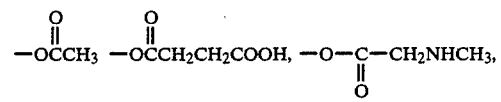

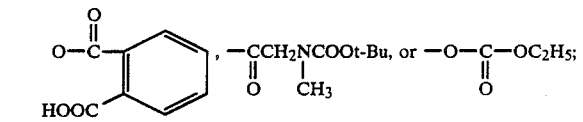

(b) C$_{1-3}$ alkoxy especially methoxy, ethoxy or i- or n-propyloxy;
(c) F or Cl;
(d) hydrogen;
(e) hydroxy; or

(f)

R$_1$ is (a) nitrogen bonded group including R'NH wherein R' is as defined below;
(b) hydrogen;
(c) hydroxy;
(d) mercapto;
(e) substituted oxy;
(f) substituted thio;
(g) hydrocarbyl or substituted hydrocarbyl group;
(h) cyano;
(i) carbonyl or thiocarbonyl containing substituents bonded by said carbonyl or thiocarbonyl radical;
(j) halo;
(k) phosphono or a substituted phosphono group.

When $R_1$ is R'NH—, R' represents a substituted or unsubstituted aliphatic, aromatic or heterocyclic, araliphatic or heterocyclylaliphatic carboxylic acid radical or a carbothioic acid radical such as the acyl radicals of the known cephalosporins and penicillins. These acyl radicals can be represented by the general formula

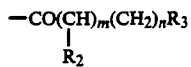

where $R_2$ is a radical of the group defined below, m and n represent 0–4 and $R_3$ represents R" or ZR", which are also defined below.

One group of the acyl radicals, i.e., when m and n are both 0 and $R_3$ is R", can be represented by the general formula

wherein R" is:
(a) straight or branched chain alkyl having from 1 to 20 carbon atoms especially methyl, trifluoromethyl, ethyl, isopropyl, t-butyl, pentyl or hexyl;
(b) aryl having from 6 to 10 carbon atoms especially phenyl, substituted phenyl or naphthalene;
(c) cycloalkyl having from 3 to 8 carbon atoms especially cyclopentyl, or cyclohexyl;
(d) alkenyl having from 2 to 20 carbon atoms especially $C_{2-6}$alkenyl such as vinyl, allyl, or butenyl;
(e) cycloalkenyl having from 5 to 8 carbon atoms especially cyclopentenyl or cyclohexenyl;
(f) alkynyl having from 2 to 20 carbon atoms especially $C_{2-6}$alkynyl for example, ethynyl, propynyl or hexynyl;
(g) alkoxy having from 1 to 10 carbon atoms especially $C_{1-3}$ alkoxy such as methoxy, ethoxy or n-propoxy or i-propoxy;
(h) aralkyl, alkaryl, aralkenyl, aralkynyl, alkenylaryl or alkynylaryl wherein alkyl, aryl, alkenyl and alkynyl are as previously defined;
(i) monoheteroaryl, di- or polyheteroaryl, or fused heteroaryl containing from 1 to 3 of any one or more of the heteroatoms N, S or O in each heteroaryl ring thereof, for example, pyridyl, pyrryl, thienyl, isothiazolyl, imidazolyl, pyrazinyl, pyrimidyl quinolyl, isoquinolyl, benzothienyl, isobenzofuryl pyrazolyl, indolyl, purinyl, carbozolyl, isoxazolyl and the like;
(j) heteroarylalkyl such as 2-pyridylmethyl, 2-thienylmethyl and 3-isothiazolylethyl; or
(k) hydrogen.

The above groups (a)–(b) can be unsubstituted or can be substituted by radicals such as alkyl, alkoxy, halo such as fluoro, chloro, bromo or iodo, cyano, carboxy, alkylsulfoamino, carbamoyl, alkyl or aminosulfonyl, azido, amino, substituted amino such as monoalkylamino and dialkylamino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is methoxy, ethoxy, benzyl, p-hydroxybenzyl, 3- or 4-nitrobenzyl, p-aminobenzyl, o-aminobenzyl, m-aminobenzyl, o-sulfobenzyl, p-carboxymethylbenzyl, p-carbamoylmethylbenzyl, m-fluorobenzyl, m-bromobenzyl, p-chlorobenzyl, p-methoxybenzyl, p-aminomethylbenzyl, hydrogen, methyl, ethyl, cyanomethyl, 2-pentenyl, n-amyl, n-heptyl, phenethyl, difluoromethyl, trifluoromethyl, dichloromethyl, dibromoethyl, 1-(3-methylimidazolyl)-methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)methyl, 2- or 3-(5-sulfothienyl)-methyl, 2- or 3-(5-carboxythienyl)methyl, 3-(1,2,5-thiadiazolyl)methyl, 3-(4-methoxy-1,2,5-thiadiazolyl)-methyl, 2-furylmethyl, 2-(5-nitrofuryl)methyl, 3-furylmethyl, 2-thienylmethyl, and tetrazolylmethyl. The term "sulfo" represents mercapto or thio, alkyl or aminosulfinyl and alkyl or aminosulfonyl.

The acyl group can also be a radical of the formula

wherein n is 0–4, Z represents oxygen, sulfur or nitrogen, and R" is defined as above. Representative members of the substituent

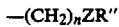

are allylthiomethyl, allylaminomethyl, phenylthiomethyl, butylmercaptomethyl, α-chlorocrotylmercaptomethyl, phenoxymethyl, phenylaminomethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)-phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-carboxymethyl)phenylthiomethyl, 2-pyrimidinylthiomethyl, phenethylthiomethyl, 1-(5,,6,7,8-tetrahydronaphthyl)oxomethyl, 6,8-bis(methylthio)octanoyl.

Furthermore, the acyl group can be a radical of the formula

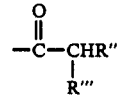

wherein R" is defined as above and R''' is a radical such as amino, hydroxy, azido, carbamoyl, guanidino, alkanoyloxy, halo, sulfamino, tetrazolyl, sulfo, carboxy, carbalkoxy, and the like. Representative members of the substituent

are α-aminobenzyl, α-amino-2-thienyl, α-methylaminobenzyl, α-amino-γ-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, D(−)-α-hydroxybenzyl, α-carboxybenzyl, α-amino-3-thienyl, α-amino-2-thienyl, D(−)-α-amino-3-chloro-4-hydroxybenzyl, D(−)-α-amino-3-thienyl, 1-aminocyclohexyl, α-(5-tetrazolyl)benzyl, α-sulfaminobenzyl, α-sulfamino-3-thienyl, α-(N-methylsulfamino)benzyl, D(−)-α-guanidino-2-thienyl, D(−)-α-guanidinobenzyl, α-guanylureidobenzyl, α-hydroxybenzyl, α-azidobenzyl, α-fluorobenzyl, 4-(5-methoxy-1,3-oxadiazolyl)aminomethyl, 4-(5-methoxy-1,3-oxadiazolyl)-hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)hydroxymethyl, 2-(5-chlorothienyl)-carboxymethyl, 3-(1,2-thiazolyl)aminomethyl, 3-(1,2-thiazolyl)hydroxymethyl, 3-(1,2-thiazolyl)-carboxymethyl, 2-(1,4-thiazolyl)thiazolyl)-carboxymethyl, 2-benzothienylaminomethyl, 2-benzothienylhydroxymethyl, 2-benzothienylcarboxymethyl, 2-azidooctyl-3-phenyl-3-azidomethyl, α-sulfobenzyl, and α-phosphonobenzyl.

Alternatively, the group

can be an unsubstituted or substituted alkyl or aryl sulfonamido group such as phenylsulfonamido, ethylsulfonamido, trifluoromethane sulfonamido, benzylsulfonamido, 2,5-dimethylsulfonamido, 4-chlorophenylsulfonamido, 4-methoxyphenylsulfonamido, or an unsubstituted or substituted alkyl or aryl sulfonylalkylamino group such as CH₃SO₂CH(CH₃)NH— or C₆H₅SO₂CH₂NH—, and the like, or hydroxyamino.

Preferably, R' is:

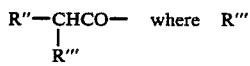

represents aryl especially phenyl or substituted phenyl; R''' is —COOCH₃ or COOCH₂C₆H₅;

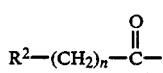

where
R² represents:
(a) hydrogen;
(b) methyl or substituted methyl such as trifluoromethyl, cyanomethyl or methoxymethyl;
(c) thienyl;
(d) phenyl; or
(e) mono- and disubstituted phenyl and thienyl wherein the substituents are selected from the group consisting of chloro, bromo, fluoro, nitro, loweralkyl, and loweralkoxy;

n is 0 or 1; or

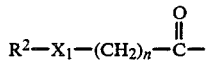

where
X₁ is oxygen or sulfur;
R² and n are as previously defined.
Even more preferably, R' is:

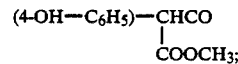

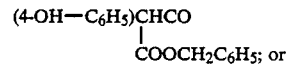

The oxy or thio substituent represented by R₁ in formula (I) can be a substituted hydroxy or mercapto group such as —XR'₁ wherein X is oxygen or sulfur and R'₁ is a hydrocarbyl group, preferably a straight or branched loweralkyl group of 1-6 carbon atoms, a straight or branched chain loweralkenyl or loweralkynyl group of 3-6 carbon atoms, a monocyclic aryl group such as phenyl, furyl, pyrryl and pyridyl, or an aralkyl group such as benzyl. These alkyl, alkenyl, alkynyl, aryl or aralkyl groups can be substituted with groups such as hydroxy, halo, nitro, amino, carboxy, thio, and the like. Other specific substituents represented by R₁ that might be mentioned are groups of the formula —OAc, —SAc, —SO₃H, —SO₂NH₂, —OCD₃, —SO₂R₂, —SO₂NR₃R₄, —OCOOR₂, —OSO₂R₂, —SOR₂, —O-COSR₂, —OCONR₃R₄, and the like wherein Ac represents an acyl group such as a formyl or loweralkanoyl, R₃ and R₄ represent hydrogen, loweralkyl, acyl and loweralkoxy, and R₂ represents loweralkyl, halolowerallkyl, aryl, aralkyl and substituted derivatives of such groups.

When R₁ is hydrocarbyl it can be straight or branched loweralkyl, straight or branched lower-alkenyl, loweralkynyl, aralkyl, cycloalkyl, a monocyclic aryl group, or a monocyclic heterocyclic group which can also be substituted with one or more groups such as halo, hydroxy, alkoxy, amino, nitro, sulfonyl, sulfamoyl, acyloxy, carbamoyloxy, carboxy, carboxamido and N-substituted carboxamido. Representative examples of such groups are C₁₋₆ alkyl such as methyl, trifluoromethyl, ethyl, n-propyl, isopropyl, t-butyl; C₂₋₆ alkenyl especially allyl, α-butenyl; C₂₋₆ alkynyl such as ethynyl and methylethynyl; loweraralkyl such as benzyl, p-methoxybenzyl, phenethyl; phenyl, p-aminophenyl; cyclopropyl, cyclopentyl and 4-hydroxycyclohexyl;

R₁ in formula (I) above may also represent cyano or a group of the general formula

wherein X' is oxygen or sulfur, and R'' is hydrogen, halo, hydroxy, mercapto, amino, substituted amino, alkyl, aryl, aralkyl, aralkoxy such as benzyloxy, alkoxy or aryloxy such as phenoxy, pyrroloxy, furyloxy, and thienyloxy, alkylthio or arylthio. Examples of these substituents are —COOH, —CSSH, —COR$_2$, —COOR$_2$, —COSR$_2$, —CSSR$_2$, —CONH$_2$, —CSNH$_2$, —CSR$_2$, —CONHR$_2$, —CSNH, —CONR$_3$R$_4$ and —CSNR$_3$R$_4$ wherein R$_2$ represents a straight or branched chain alkyl group of 1-6 carbon atoms and R$_3$ and R$_4$ represent hydrogen or R$_2$;

Furthermore, R$_1$ in formula (I) above represents a nitrogen bonded group such as amino, substituted amino groups, nitro, azido, nitroso, isocyanato, isothiocyanato and hydroxyamino. Specific examples of nitrogen bonded groups that might be mentioned are —N$_3$, —NH$_2$, —NHR$_2$, NR$_2$R$_3$, wherein R$_2$ represents a straight or branched chain loweralkyl group of 1 to 6 carbon atoms, R$_3$ represents R$_2$ or hydrogen, and n represents the integer 1 or 2.

Finally, the substituent R$_1$ in formula (I) represents phosphono or a metal or ammonium salt thereof, or a substituted phosphono group of the formula:

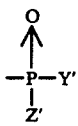

where Y' and Z' are the same or different and represent

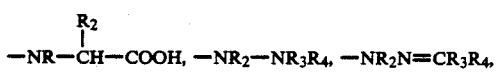

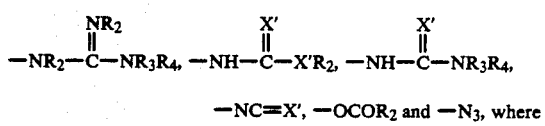

—NC≡X', —OCOR$_2$ and —N$_3$, where where
R$_2$ represents hydrogen or a hydrocarbyl radical, R$_3$ and R$_4$ represent hydrogen, hydrocarbyl, alkoxy or an acyl radical, and X' represents oxygen or sulfur.

Preferably, R$_1$ is
(1) R'NH— where R' represents acyl;
(2) OR$_1$' where R$_1$' represents hydrocarbyl group;
(3) C$_{1-6}$alkylthio; C$_{1-6}$ alkylsulfonyl;
(4) halo such as fluoro, chloro, bromo or iodo; or;
(5) hydrogen;
(6) C$_{1-6}$ alkyl.

Even more preferably, R$_1$ is
(1) R'NH where R' represents:

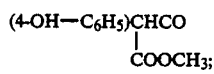  (a)

  (b)

  (c)

(2) C$_{1-3}$alkyl;
(3) OR$_1$' where R$_1$' is
(a) C$_{12-6}$ alkyl especially methyl, ethyl, n-propyl;
(b) —C$_6$H$_5$;
(c) —CH$_2$CH$_2$C$_6$H$_5$; or

  (d)

where R represents hydrogen, C$_{1-6}$alkyl, phenyl, substituted or unsubstituted benzyl, or C$_{1-6}$alkylamino such as CH$_3$NH—, C$_2$H$_5$NH—;
(4) C$_{1-6}$ alkylsulfonyl;
(5) halo especially Cl or F; or
(6) hydrogen R$_2$ is
(a) hydrogen; or
(b) loweralkoxy especially CH$_3$O.

B of Formula (I) above represents OB$_1$, or NB$_2$B$_3$ wherein B$_1$ and B$_2$ independently are:
(a) straight or branched chain alkyl having from 1 to 20 carbon atoms, ethyl, isopropyl, t-butyl, pentyl or hexyl;
(b) aryl having, from 6 to 10 carbon atoms;
(c) cycloalkyl having from 3 to 8 carbon atoms;
(d) alkenyl having from 2 to 20 carbon atoms;
(e) cycloalkenyl having from 5 to 8 carbon atoms;
(f) alkynyl having from 2 to 20 carbon atoms;
(g) alkoxy having from 1 to 10 carbon atoms;
(h) aralkyl, alkaryl, aralkenyl, aralkynyl, alkenylaryl or alkynylaryl wherein alkyl, aryl, alkenyl and alkynyl are as previously defined;
(i) loweralkenylalkyl;
(j) alkanoylalkyl;
(k) alkanoyloxyalkyl;
(l) alkoxyalkyl;
(m) alkanoyloxy;
(n) a heterocyclic group including heterocyclic alkyl or heterocyclic alkenyl.

The above groups (a)–(n) can be unsubstituted or can be substituted by radicals such as alkyl, hydroxy, alkoxy, halo, nitro, mercapto, amino, substituted amino, cyano, carboxy, sulfoamino, carbamoyl, carbamoyloxy, alkyl or amino-sulfonyl, alkyl or amino-sulfinyl, sulfamoyl, azido, amino such as mono or dialkylamino, substituted amino, carboxamido or N-substituted carboxamido; and B$_3$ is hydrogen or B$_1$.

Representative examples of such groups are C$_{1-6}$alkyl especially methyl, ethyl or t-butyl, allyl, 3-butenyl, methoxyethyl, benzyl, p-carbomethoxybenzyl, m-carbomethoxybenzyl, p-sulfonylbenzyl, m-fluorobenzyl, o,p-dinitrobenzyl, o,p-dichlorobenzyl, p-methylbenzyl, m-methoxybenzyl, o-methylthiobenzyl, benzhydryl, CH$_2$CH$_2$CH$_2$COOCH$_3$, —CH$_2$COOC$_2$H$_5$, and the like.

Preferably, B$_1$ and B$_2$ independently are substituted or unsubstituted
(1) aralkyl;
(2) aryl;
(3) straight or branched loweralkyl;
(4) straight or branched loweralkenyl;
(5) cycloalkyl;
(6) alkanoyloxyloweralkyl;
(7) alkanoylloweralkyl;
(8) alkoxyloweralkyl; or
(9) haloalkyl; and
B$_3$ is hydrogen or B$_1$.

Even more preferably, B$_1$ and B$_2$ independently are substituted or unsubstituted
(1) benzyl;
(2) ethyl;
(3) t-butyl;
(4) —CH$_2$CH$_2$CH=CH$_2$ or CH$_2$—CH=C(CH$_3$)$_2$;

(5) —CH$_2$CH$_2$CH$_2$COOt-Bu;
(6) alkanoyloxymethyl; or
(7) alkanoylmethyl; and B$_3$ is hydrogen or B$_1$.

Q in formula (I) represents
(1) hydrogen;
(2) C$_{1-6}$ alkyl especially methyl, ethyl, isopropyl, n-pentyl or n-hexyl;
(3) halo;
(4) hydroxy;
(5) loweralkoxy;
(6) aryloxy especially phenoxy;
(7) benzyl;
(8) phenylthio;
(9) phenyl;
(10) loweralkylthio; or
(11) —COR.

Preferably Q is
(1) hydrogen;
(2) C$_{1-6}$alkyl;
(3) chloro or fluoro;
(4) unsubstituted or substituted phenylthioC$_{1-6}$alkyl or phenylsulfonyl C$_{1-6}$alkyl.
(5) hydroxy;
(6) phenoxy;
(7) CH$_3$O;

Even more preferably, Q is
(1) hydrogen;
(2) methyl, ethyl or i- or n-propyl.

B: Preparation of the Compounds Within the Scope of the Present Invention

The 1-oxa-dethia cephalosporin esters of formula (I) where OB$_1$ is other than hydroxy can be prepared from the corresponding acid according to conventional methods of esterification. For example, (1) A compound of formula (I) is treated with a lower alkanol, a substituted or unsubstituted benzyl alcohol, or a substituted or unsubstituted benzhydrol (diphenylmethanol) in the presence of a catalyst and any one or a combination of those illustrated below in Table I.

TABLE I

Catalysts for Esterification (1) Hydrochloric acid or hydrobromic acid
(2) Sulfuric acid
(3) C$_{1-3}$alkanoic acid e.g. acetic acid
(4) Phosphoric acid
(5) Trifluoroacetic acid or anhydride
(6) Trichloroacetic acid
(7) p-Toluenesulfonic acid or other arylsulfonic acids
(8) Acidic ion-exchange resins with calcium sulfate
(9) Polymer-protected aluminum chloride, e.g., a complex between anhydrous aluminum chloride and polystyrene-divinyl benzene copolymer diphenylphosphitepyridine
(10) A Lewis acid such as boron trifluoride
(11) Aromatic sulfonylchloride-pyridine, e.g., p-toluenesulfonylchloride
(12) triphenylphosphine ditriflate
(13) dicyclohexylcarbodiimide (DCCD)
(14) β-trichloromethyl-β-propiolactone
(15) N,N'-carbonyldimidazole
(16) triphenylphosphine diethylazodicarbonylate
(17) 6-chlorobenzensulfonyloxybenzotriazole
(18) 1-methyl-2-halopyridinium iodide-tertiary amine (e.g., triethylamine).

at from about 0° to about 150° C. with or without refluxing until the esterification is substantially complete. Optionally, a solvent may be used to facilitate the reaction. The common solvents used are benzene, toluene, xylene, sulfolane-xylene, diethylether, tetrahydrofuran, 1,2-dimethoxyethane, dioxane and the like;

(2) A compound of formula (I) is converted to an acid halide such as acid chloride or bromide via treatment with a halogenating agent such as thionyl chloride, phosphorus penta- or oxychloride followed by reaction with an appropriate alcohol; and (3) Other methods such as alkylation of carboxylate salts (e.g., K$^+$, Na$^+$, Ca$^{++}$, Ag$^+$, Cu$^+$, tetraalkylammoniumR$_4$N$^+$, and Hg$^{++}$ salts) of formula (I) with alkyl halides, for example, benzylchloride, benzyhydryl chloride; reaction with alkyl isoureas; treatment with diazomethane or diazophenylmethane (C$_6$H$_5$CHN$_2$); alcoholysis of anhydride derived from the cephalosporin acid corresponding to formula (I); transformation with alkyl t-butyl ethers; and the like may also be used. These methods are disclosed in Saul Patai, editor, *The Chemistry of Functional Groups*, Supplement B, *The Chemistry of Acid Derivatives*, pp. 411-436, John Wiley & Sons, Chichester-New York-Brisbane-Toronto, 1979, and are incorporated herein by reference.

The 1-oxa-dethia cephalosporin free acids and the syntheses thereof are known. For example, the following references provide general synthetic methods for various 1-oxa-dethia cephalosporin derivatives and are incorporated herein by reference:

L. D. Cama & B. G. Christensen, *J. Am. Chem. Soc.*, 96, 7582 (1974).
S. Uyeo et al., *J. Am. Chem. Soc.*, 101, 4403 (1979).
M. Narisada et al., *J. Med. Chem.*, 22, 757 (1979).
M. Aratani et al., *J. Org. Chem.*, 45, 3682 (1980).
H. Yanagisawa & A. Ando, *Tet. Lett.*, 1982, 3379.
M. Yoshioma, *Tet. Lett.*, 1980, 351.

As the compounds referred to in this invention can be organic acids, their pharmaceutically acceptable salts are those resulting from the neutralization of the acid with a base. The base employed is usually an inorganic base, for example, an alkali metal hydroxide such as sodium hydroxide, potassium or sodium carbonate, potassium or ammonium hydroxide, or other hydroxides or carbonates of aluminum, calcium, lithium, magnesium or zinc. An organic base such as triloweralkyl amine, for example, triethylamine, tributylamine and tricyclohexylamine; benzothine; chloroprocaine; choline; diethanolamine; ethylenediamine; meglumine; or procaine, is also commonly used. Generally the neutralization is conducted in an inert solvent such as water; a C$_{1-3}$ alkanol such as methanol, ethanol or isopropanol; a C$_{3-6}$ ketone such as acetone, or ethylmethyl ketone; an ethereal solvent such as diethyl ether, tetrahydrofuran or dioxane; acetonitrile; or an aromatic solvent such as toluene. Mixtures of the above described solvents are also employed. Generally the neutralization is carried out in aqueous ethanol, at 0°-75° C., preferably at 0°-25° C., followed by filtration to collect the salts.

C. Utility of the compounds within the scope of the invention

This invention also relates to a method of treatment for patients (or mammalian animals raised in the dairy, meat, or fur industries or as pets) suffering from inflammation or pain. More specifically, it relates to a method of treatment involving the administration of a compound of formula (I) as the active constituent.

For the treatment of inflammation and pain a compound of formula (I) may be administered orally, topically, parenterally, by inhalation spray or rectally in dosage unit formulations containing conventional non-toxic pharmaceutically acceptabl carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients ma also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
 (1) suspending agents such as sodium carboxymethylcellulose, methylcellulose, hydroxypropylmethylcellulose, sodium alginate, polyvinylpyrrolidone, gum tragacanth and gum acacia;
 (2) dispersing or wetting agents which may be
 (a) a naturally-occurring phosphatide such as lecithin,
 (b) a condensation product of an alkylene oxide with a fatty acid, for example, polyoxyethylene stearate,
 (c) a condensation product of ethylene oxide with a long chain aliphatic alcohol, for example, heptadeca ethyleneoxycetanol,
 (d) a condensation product of ethylene oxide with a partial ester derived from a fatty acid and a hexitol such as polyoxyethylene sorbitol monooleate, or
 (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are coco butter and polyethylene glycols.

For topical use, creams, ointments, jellies, solutions or suspensions, etc., containing the anti-inflammatory agents are employed.

D. Biological evidence in support of utility of the invention

It has been found that the compounds of Formula (I) have anti-inflammatory antidegeneration activity and are effective in the prevention and inhibition of edema and granuloma tissue formation as shown below in Table II by the effective inhibition of the proteolytic function of human granulocyte elastase.

TABLE II

| $R_1$ | $R_2$ | M | B | $ED_{50}$ (μg/ml) |
|---|---|---|---|---|
| 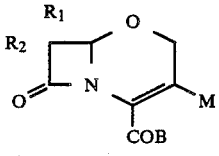 | | | | |
| (4-OH—$C_6H_5$)CHCONH COOCH$_3$ | OCH$_3$ | —CH$_2$S-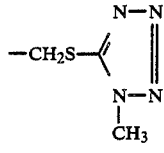 | OCH$_3$ | ≧20 |
| (4-OH—$C_6H_5$)CHCONH COOCH$_2$C$_6$H$_5$ | OCH$_3$ | —CH$_3$ | OCH$_2$C$_6$H$_5$ | 17 |
| C$_6$H$_5$CONH | H | —CH$_3$ | OCH$_2$C$_6$H$_5$ | 20 |
| 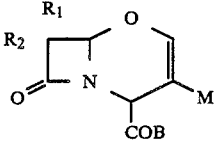 | | | | |
| C$_6$H$_5$CONH | H | —CH$_3$ | OCH$_2$C$_6$H$_5$ | 5 |

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 2.5 to about 75 mg of the compound per kilogram of body weight per day (about 75 mg to about 3.75 gms per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

PROTOCOL

Enzyme Assays for the Inhibition of Human Polymorphonuclear Leukocyte Elastase Via Hydrolysis of N-t-Boc-alanyl-alanyl-prolylalanine-p-nitroanilide Reagents 0.05 M TES (N-tris[hydroxymethyl]methyl-2-aminoethanesulfonic acid) Buffer, pH 7.5.

0.2 mM N-t-Boc-alanyl-alanyl-prolyl-alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (cephalosporin sulfone esters) to be tested dissolved in DMSO just before use.

Assay Procedure

To 1.0 ml of 0.2 mM Boc-AAPAN in a cuvette, 0.01–0.1 ml of DMSO with or without inhibitor was added. After mixing, a measurement was taken at 410 mμ to detect any spontaneous hydrolysis due to presence of test compound. 0.05 Milliliters of PMN extract was then added and the ΔOD/min at 410 mμ was measured and recorded. Beckman model 35 spectrophotometer was used.

Results

Results were reported as ED$_{50}$, i.e., effective dosage in micrograms per milliliter (μg/ml) for 50% inhibition of the enzyme activity 2 minutes after zero time.

Comments

The elastase activity in the crude PMN extract may vary from one preparation to another. A control of each new batch is run, and the volume added in the assay procedure is adjusted according to activity.

What is claimed is:

1. A pharmaceutical composition for treating elastase-mediated diseases in a mammalian species comprising a non-toxic pharmaceutical carrier and an effective amount of a compound of structural formula:

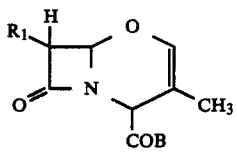

wherein R$_1$ is

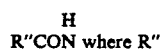

represents phenyl or substituted phenyl; and B is OB$_1$ wherein B$_1$ is C$_{1-6}$ alkyl, benzyl or substituted benzyl.

2. The pharmaceutical composition of claim 1 wherein the active compound is

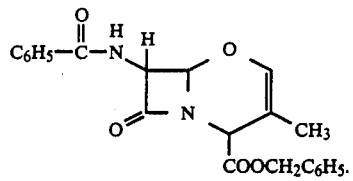

3. A method of treating elastase-mediated diseases comprising the administration to a mammalian species in need of such treatment an effective amount of a compound of structural formula:

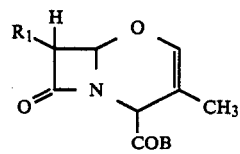

wherein R$_1$ is

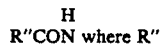

represents phenyl or substituted phenyl; and B is OB$_1$ wherein B$_1$ is C$_{1-6}$ alkyl, benzyl or substituted benzyl.

4. The method of claim 3 wherein the active compound is

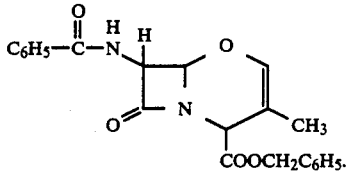

* * * * *